United States Patent [19]
Schilperoort et al.

[11] Patent Number: 5,464,763
[45] Date of Patent: * Nov. 7, 1995

[54] PROCESS FOR THE INCORPORATION OF FOREIGN DNA INTO THE GENOME OF DICOTYLEDONOUS PLANTS

[75] Inventors: Robbert A. Schilperoort; Andreas Hoekema, both of Leiden, Netherlands

[73] Assignees: Rijksuniversiteit Leiden; Robbert Adriaan Schilperoort, both of Leiden, Netherlands

[*] Notice: The portion of the term of this patent subsequent to Jul. 10, 2007, has been disclaimed.

[21] Appl. No.: 173,271

[22] Filed: Dec. 23, 1993

Related U.S. Application Data

[63] Continuation of Ser. No. 550,736, Jul. 9, 1990, abandoned, which is a continuation of Ser. No. 583,022, Feb. 23, 1984, Pat. No. 4,940,838.

[30] Foreign Application Priority Data

Feb. 24, 1983 [NL] Netherlands ............................ 8300698

[51] Int. Cl.$^6$ ............................ C12N 15/84; C12N 1/21; C12N 15/74
[52] U.S. Cl. ................................... 435/172.3; 435/240.4; 435/252.3; 435/320.1; 800/205; 935/30; 935/56; 935/67
[58] Field of Search ............................ 435/172.3, 240.4, 435/320.1, 252.3; 800/205; 935/30, 56, 67

[56] References Cited

U.S. PATENT DOCUMENTS

| | | | |
|---|---|---|---|
| 4,459,355 | 7/1984 | Cello et al. | 435/172.3 |
| 4,536,475 | 8/1985 | Anderson | 435/172.3 |
| 4,940,838 | 7/1990 | Schilperoort et al. | 800/205 |

FOREIGN PATENT DOCUMENTS 0116718  8/1984  European Pat. Off. ........ C12N 15/00

OTHER PUBLICATIONS

Jen et al, Proc. Natl. Acad. Sci. USA 83, 3895–3899 (1986).
De Framond et al, Bio/Tech 1, 262–269 (1983).
Chilton, et al; Cloning Vectors for Plant Gen. Eng; First Eur. Cong. on Cell Bio, 1982.
Programme from Structure and Function of Plant Genames Course Port Portege, Italy, 1982.
Barton et al, Tobacco Plants Regenerated from Cells Transformed With an Engineered Ti–Plasmid Contain the Gene Yeast Alcohol DehydrogenaseI, Encoding, National Febs Conference, Port Portese, Italy, 1982.
Bevan, et al, 1982, Journal of Molecular and Applied Genetics, pp. 539–546.
Schell, et al Ti–Plasmids as Experimental Gene Vectors for Plants, Miami Winter Symposia, vol. 20, pp. 191–209, 1983.
Michelmore et al 1987, Transformation of Lettuce (*Lactuca scotiva*) Mediated by Agrobacterium Tumefaciens pp. 439–442.
Guri, et al 1988, J. Plant Physiol, Agrobacterium Transformation of Eggplant 133: 52–55.
Third Annual Midwest Crown Gall Conference, St. Louis, Mo., Nov. 20–21, Presentation by Annick de Framond entitled "Mini–Ti plasmid complementation in trans by a neiper Ti plasmid"(Program).
Fifteenth Miami Winter Symposium, 17–21 Jan. 1983, Presentation by Mary–Dell Chilton entitled "Ti and Ri Plasmids as Vectors for Genetic Engineering", renamed at the lecture Mini–Tiplasmid and a Chimeric Gene Construct: New Approaches to Plant Gene Vector Construction Program 1982 pp. 14–15.
Hille et al 1981 Plasmid 6: 151–154.
Hooykaas et al 1980 Plasmid 4: 64–75.
Machida et al. 1982. PNAS USA 79: 277–281.
deFramond 21 Jan 1983 Theses (Dissertation) presented at L'Institut National Agrencrnique Paris–Grignon.
Garfinkel et al 1981 Cell 27: 143–153.
Hockerma et al 1983. Nature 303: 179–180.
Hille et al 1982, Plasmid 7: 107–118.
Doms et al 1982, Nature 295: 432–434.
Leemans et al 1982. EMBO J. 1: 147–152.
Yadau et al 1982 Proc. Natl Acad Sci USA 79: 6322–6326.
Iyer et al. 1982. Mol. Gen. Genet. 188: 418–424.
Bevan et al 1982. Ann Rev Genet 16: 357–384.

*Primary Examiner*—Patricia R. Moody
*Attorney, Agent, or Firm*—Ladas & Parry

[57] ABSTRACT

The invention relates to a process for the incorporation of foreign DNA into chromosomes of dicotyledonous plants by infecting the plants or incubating plant protoplasts with *Agrobacterium bacteria*, which contain one or more plasmids, wherein bacteria are used which contain at least one plasmid having the vir-region of Ti (tumor inducing) plasmid but no T-region, and at least one other plasmid having a T-region with incorporated therein foreign DNA but no vir-region, as well as to a *Agrobacterium bacteria*, suitable for use in the process according to claim 1 wherein at least one plasmid which has the vir-region of a Ti (tumor inducing) plasmid but no T-region and at least one other plasmid which has a wild type T-region with incorporated in it foreign DNA but no vir-region.

12 Claims, 3 Drawing Sheets

PROCESS FOR THE INCORPORATION OF FOREIGN DNA INTO THE GENOME OF DICOTYLEDONOUS PLANTS

This is a continuation of copending application Ser. No. 07/550,736, filed on Jul. 9, 1990, now abandoned, which is a continuation of application Ser. No. 06/583,022, (now U.S. Pat. No. 4,940,838), filed Feb. 23, 1984.

A process for the incorporation of foreign DNA into the genome of dicotyledonous plants; *Agrobacterium tumefaciens* bacteria and a process for the production thereof; plants and plant cells with modified genetic properties; a process for the preparation of chemical and/or pharmaceutical products.

The invention relates to a process for the incorporation of foreign DNA into the genome of dicotyledonous plants by infecting the plants or by incubating plant protoplasts with *Agrobacterium tumefaciens* bacteria, which contain one or more plasmids.

It is known that the Ti plasmid of *A. tumefaciens* is essential for the capacity of this bacterium to cause the formation of so-called "Crown gall" tumours on dicotyledonous plants (Van Larebeke et al, *Nature* (London) 252, 169–170 (1974); Watson et al, *J. Bacteriol.* 123, 255–264 (1975); Zaenen et al, *J. Mol. Biol.* 86, 109–127 (1974)). Part of this plasmid, designated as the T-region, is integrated as T-DNA in the plant genome (the chromosomal DNA) during tumour induction (Chilton et al, *Cell* 11, 263–261 (1977); Chilton et al, *Proc. Nat. Acad. Sci. U.S.A.* 77, 4064–4068 (1980)., Thomashow et al, *Proc. Nat. Acad. Sci. U.S.A.* 77, 6448–6452 (1980); Willmitzer et al, Nature (London) 287, 259–361 (1980) and is expressed in various RNA transcripts (Drummond et al, *Nature* (London) 269, 535–536 (1977); Ledeboer, thesis State University of Leyden (1978); Gurley et al, *Proc. Nat. Acad. Sci. U.S.A.* 76, 2828–2832 (1979); Willmitzer et al, *Mol. Gen. Genet.* 182, 255–262 (1981)). The tumour cells show a phyto-hormone independent growth and contain one or more unusual aminoacid derivatives, known as opines of which octopine and nopaline are best-known. The T-DNA originating from an octopine Ti plasmid carries a gene, which codes for the enzyme lysopine dehydrogenase (LpDH) or octopine synthase (OCS) which the tumour cell needs for the synthesis of octopine (Schröder et al, *FEBS Lett.* 129, 166–168 (1981)). The plasmid furthermore contains genes for the use of these opines by the bacterium (Bomhoff et al, *Mol. Gen. Genet.* 145, 177–181 (1976); Montoya et al, *J. Bacteriol.* 129, 101–107 (1977)). If the T-region of the plasmid is lacking, no tumours are induced (Koekman et al, *Plasmid* 2, 347–357 (1979)). In addition to the T-region another region of the Ti plasmid appears to be essential for the tumour inducing capacity of the bacterium (Garfinkel et al, *J. Bacteriol.* 144, 732–743 (1980); Ooms et al, *J. Bacteriol.* 144, 82–91 (1980)), which part, however, has never been found in the plant tumour cells. This region with a size of about 20 Md, in which mutations appear to be complementary in trans, is called the vir (virulence) region (Hille et al, *Plasmid* 6, 151–154 (1981)); Hille et al, *Plasmid* 7, 107–118 (1982); Klee et al, *J. Bacteriol.* 150, 327–331 (1982).

It will be clear from the above that the procaryotic bacterium *A. tumefaciens* has a system for genetic manipulations of eucaryotic plants present in nature. The T-region of the Ti plasmid appears to be suitable for incorporating foreign DNA, in particular genes which code for particular desirable properties, into the genome of plant cells, the more so as in principle it is possible to eliminate the genes which are the cause of the tumour without simultaneously blocking the incorporation of the new genes. A first possibility seems to be to transform plant cells by infecting plants with *A. tumefaciens* bacteria which contain one or more Ti plasmids the T-region of which is manipulated in the desirable manner. It is even better to incubate plant protoplasts with such *A. tumefaciens* bacteria. For practical reasons the introduction of new genes in the T-region by means of recombinant-DNA techniques are preferably carried out in *Escherichia coli*. However, the Ti plasmid normally cannot be maintained in *E. coli* (it does not replicate in this host). So, in the existing procedures a so-called shuttle vector is used which replicates in *E. coli* and *A. tumefaciens* and into which the T-region is introduced. Subsequently new genes are introduced into this T-region; however, the complete Ti plasmid is necessary in order to transform cells via *A. tumefaciens*. The reason is that the Ti plasmid contains the essential vir-region on which genes are positioned which see to a selection of T-region (presumably by recognition of base sequences at the extremities of this T-region and the transfer to the plant.

Since the Ti plasmid does not maintain its position in *E. coli* in the existing procedures the shuttle vector with the manipulated T-region is transferred to an *A. tumefaciens* which contains a complete Ti plasmid which can co-exist with the shuttle vector. Since the shuttle vector contains T-region parts which are also present in the T-region of the Ti plasmid a double crossing-over between the homologous parts of both T-regions is forced. Therewith the new genes are incorporated into the T-region of the intact Ti plasmid.

Existing procedures for site location directed mutations of the Ti plasmids are described by Leemans et al, *The Embo Journal* 1, 147–152 (1982); Matzke et al, *J. Mol. Appl. Genet.* 1, 39–49 (1981); vide for the general principle on which these techniques are base, Ruvkun et al, *Nature* (London), 289, 85–88 (1981). The last step of the Ti plasmid mutation is always performed in Agrobacterium itself, because the host range of Ti plasmids is restricted to Rhizobiaceae. After a clones fragment of the Ti plasmid in *E. coli* has been mutated, for instance by insertion of a transposone, the mutated fragment is subcloned on a vector with a broad host range and transferred into a Ti plasmid containing Agrobacterium strain. Herein the inserted DNA is incorporated by homologous recombination via double crossing-over into the Ti plasmid, whereupon either the plasmid with a broad host range is destroyed by means of an incompatible plasmid or the Ti plasmid is transferred to another Agrobacterium by conjugation. By investigation of the transconjugants it is checked whether the correct mutation of the Ti plasmid has taken place.

These known procedures are rather laborious and give technical problems, which could be avoided of the site directed mutation of the Ti plasmid itself could directly be performed in *E. coli*. However, the Ti plasmid is lacking an origin of replication or a replicator which can function in *E. coli*.

Surprisingly, it has now been found that the desirable transfer of DNA from *A. tumefaciens* bacteria into plant cells, in which the transferred DNA is incorporated into the genome, cal also be realised if the required vir and T-regions are positioned on two different plasmids.

The process according to the invention is characterised in that Agrobacterium bacteria strains are used, which contain at least one plasmid which has the vir region of a Ti (tumour inducing)plasmid but has no T-region, and at least one other plasmid which has a T-region with foreign DNA incorporated in it but has no vir region.

If it required not to have plantcells with a tumurous character, the oncogenes (one-genes) and other sequences between the border sequences of the wild-type T-region can be taken out leaving behind an artificial T-region which comprises the foreign DNA in betwee T-region border sequences. The border sequences are defined as those sequences at the extremities of a T-region that are required for transfer and integration of T-DNA in plant chromosomes via Agrobacterium.

The invention presents new Agrobacterium strains, suitable for use in the above-mentioned process according to the invention, which are characterised in that the Agrobacterium bacteria contain at least one plasmid which has the vir region of a Ti (tumour inducing) plasmid but has no T-region, and at least one other plasmid which has a T-region with foreign DNA incorporated in it but has no vir region. Herein, T-region stands for any DNA transferred and integrated into chromosomal DNA of plants.

The new Agrobacterium strains according to the invention can be produced by incorporating into *Escherichia coli* foreign DNA in the T-region of a plasmid which contains a T-region and a replicator having a broad host range and introducing the resulting plasmid into Agrobacterium bacteria which contain at least one plasmid which has the vir region of a Ti plasmid but has no T-region.

The invention also provides plants and plant cells which have been obtained after the genetic properties of the original plants c.q. plant cells have been modified with application of the process according to the invention.

The use of the process according to the invention in which plants or plant cells with modified genetic information are obtained may be present in the improvement of plants (cultivation of an improved species, which for instance is better resistant to herbicides), as well as in the realisation of a bioreactor for fermentation of plant cells optionally immobilised thereupon, which produce a specific desirable translation product, for instance enzyme, or a secondary metabolite of the plant cell, in large quantities.

The process according to the invention therefore offers the possibility to manufacture mutants of higher plants having well defined genetically improved resp. modified properties in an otherwise unchanged background. As already remarked before this is vital to the plant breeding industry, the more so as from the tissue lines which are obtained with application of the process according to the invention regenerates can be obtained at an early stage after transformation. Furthermore, the cells with autotrophic growth, which are obtained with application of the process according to the invention, for instance the Crown gall cells, only need a very simple synthetic medium for a good growth in a fermentator, to which medium no phyto/hormones need to be added. Cells thus obtained, in which foreign DNA is introduced, can be cultured on a large scale, for the production of those substances, for which the foreign DNA codes, such as alkaloids, aminoacids, hydrocarbons, proteins, enzymes, steroids, etc. (cf. Impact of Applied Genetics, Micro-Organisms, Plants and Animals; OTA Report, Congress of the United States Office of Technology Assessment, Washington, 1981).

According to the invention Agrobacterium strains are used c.q. produced, which contain two different compatible plasmids. One plasmid contains the vir-region, but is lacking a T-region so that it has no tumour inducing capacity as such. The other plasmid carries the manipulated T-region, so that this plasmid has not tumour inducing capacity as such either. An Agrobacterium strain, which accomodates both plasmids, however, has a normal tumour inducing capacity or more in general has the capacity to incorporate DNA into the chromosomes of dicotyledonous plants, such as tomatoes, tobacco, petunia, potato, sugar beet, sunflower, leguminous plants, and the like.

The invention makes it possible that for the construction of plasmid with a T-region but without a vir-region such a small size of vector plasmid is used that the required genetic manipulations can easily be accomplished in *E. coli* as a host. When the plasmid obtained herewith is transferred to an Agrobacterium strain, which accomodates the plasmid with the vir-region but no T-region, the possibility is opened to introduce the manipulated T-region into the plant cells. The binary vector system according to the invention for genetic manipulations of plant cells eliminates the necessity to use an intact Ti plasmid therefor, with all the drawbacks connected therewith. Also, a forced crossing-over which may give rise to complications is no longer necessary according to the invention.

By the omission of the necessity to apply forced crossing-over for introducing a new gene or genes into the T-region of the intact Ti plasmid the binary vector system moreover has the advantage that it is no longer necessary to incorporate undesirable genes, including e.g. the onc-genes or parts thereof, of the T-region together with the new gene or genes into plant chromosomes. With the binary vector system it now has become possible to construct a complete "artificial" T-region such as for instance described in FIG. 5 and then to incorporate this DNA into chromosomes.

The invention is illustrated hereinunder with the aid of the drawing in which

Also examples of experiments are described, in which actually with the invention thus described both a new gene has been manipulated in the T-region and transferred to the plant cell and a completely "artificial" T-region was used with the same purpose.

Figure 1:
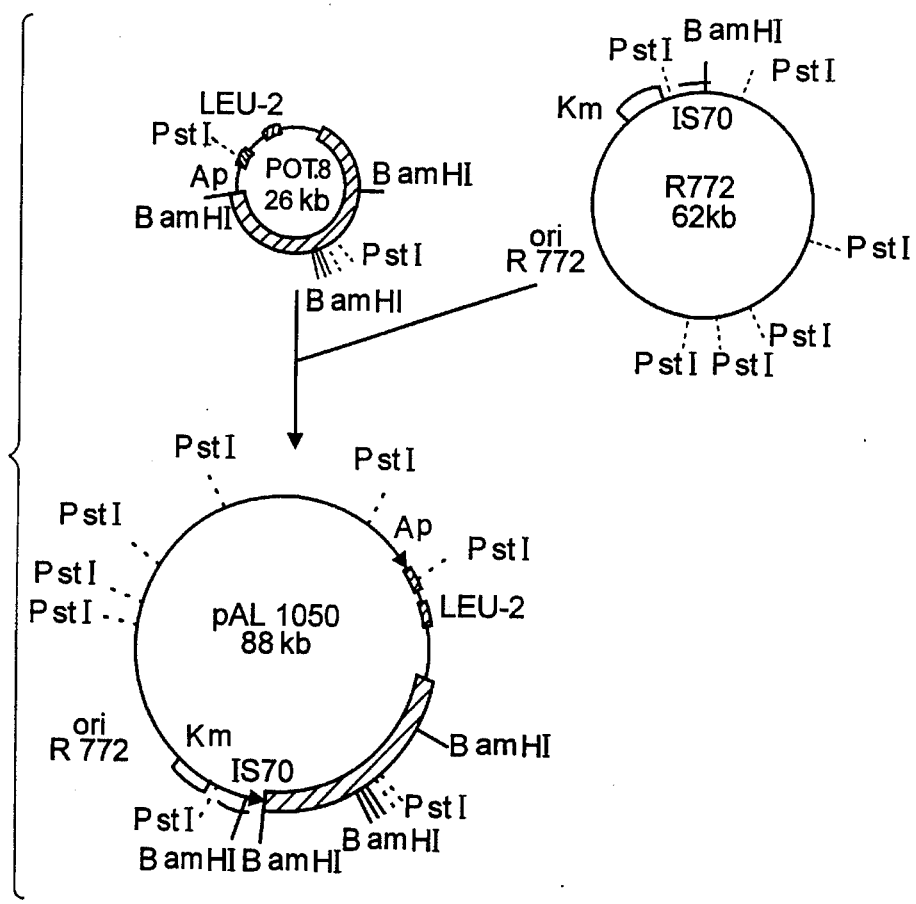
FIG. 1 shows in outline the construction of the plasmid pAL1010.

In order to obtain a plasmid which contains the intact T-region of the octopine Ti plasmid pTiAch5 and both in *A. tumefaciens* and in *E. coli* is capable of autonomous replication, use has been made of the recombinant plasmid POTY8. This plasmid is a derivative of the plasmid pJDB207 (Beggs, Molec. Genet. in *Yeast, Alfred Benson Symp.* 16, 383–389 (1981)), obtained by inserting the T-region of pTiAch5 into the locus for tetracycline resistance. This plasmid POTY8 furthermore contains as genetic markers the ampicillin resistance gene (Ap) of the plasmid pAT153 (Twigg et al, *Nature* 283, 216–218 (1980)) as well as a LEU-2 gene. The plasmid POTY8 is shown in outline in FIG. 1. The recognition sites for the restriction enzymes PstI and BamHI are indicated herein.

Since this plasmid cannot replicate in A. tumefaciens bacteria, the plasmid has been converted into a plasmid having a broad host range by fusion with the IncP plasmid R772. For this purpose R772 was introduced into the strain HB101 (with plasmid POTY8) by conjugation, whereupon transconjugants of this crossing were used as donors in further crossings with the *A. tumefaciens* strains LBA202. Transconjugants hereof were selected for the presence of the ampicillin resistance marker of POTY8. As was expected, these strains would contain a cointegrate plasmid of POTY8 and R772, because POTY8 itself is not conjugative and cannot replicate in Agrobacterium. The introduction of R772 could have taken place either in the vector part or the T-region part of POTY8. In order to be able to carry out complementation experiments, only a cointegrate containing an intact T-region is of importance. That is why subsequently 30 transconjugants were conjugated with the E. coli strain JA221 (C600 trpE leu B, vide Beggs, Nature 275, 104–109 (1978)), whereupon the progeny was examined for leucin auxotrophy. One of the 30 transconjugant strains appeared not to grow on a minimum medium without leucin added. Probably, this strain contained a R772:: POTY8 cointegrate plasmid, in which the expression of the gene LEU-2 had been inactivated by the incorporation of R772. Analysis of restriction endonuclease patterns of the R772:: POTY8 plasmid, which was called pAL1050, showed that the plasmid pAL1050 had an insertion of R772 in the pJDB207 part of POTY8, whereas the T-region had remained unmodified. The structural organisation was further confirmed by hybridisation experiments using the Southern blot technique (Southern, J. Mol. Biol. 98, 503–518 (1975)) and of labelled plasmid DNA of R772 and POTY8. The plasmid pAL1050 and the way in which it is manufactured, are shown in outline in FIG. 1. Herein the T-region is indicated in shading. One of the two copies of the insertion sequence IS70 got partly lost, which accounts for the surprising stability of the cointegrate plasmid pAL1050 found.

The plasmid pAL1050 was introduced into a non-oncogenous Agrobacterium strain (cured of its Ti plasmid), whereupon it was investigated whether by this introduction of pAL1050 the tumour inducing capacity of the strain could be restored. In conformity with expectations (the vir-region is lacking!) this appeared not to be the case, as may appear from the following table.

Figure 2:
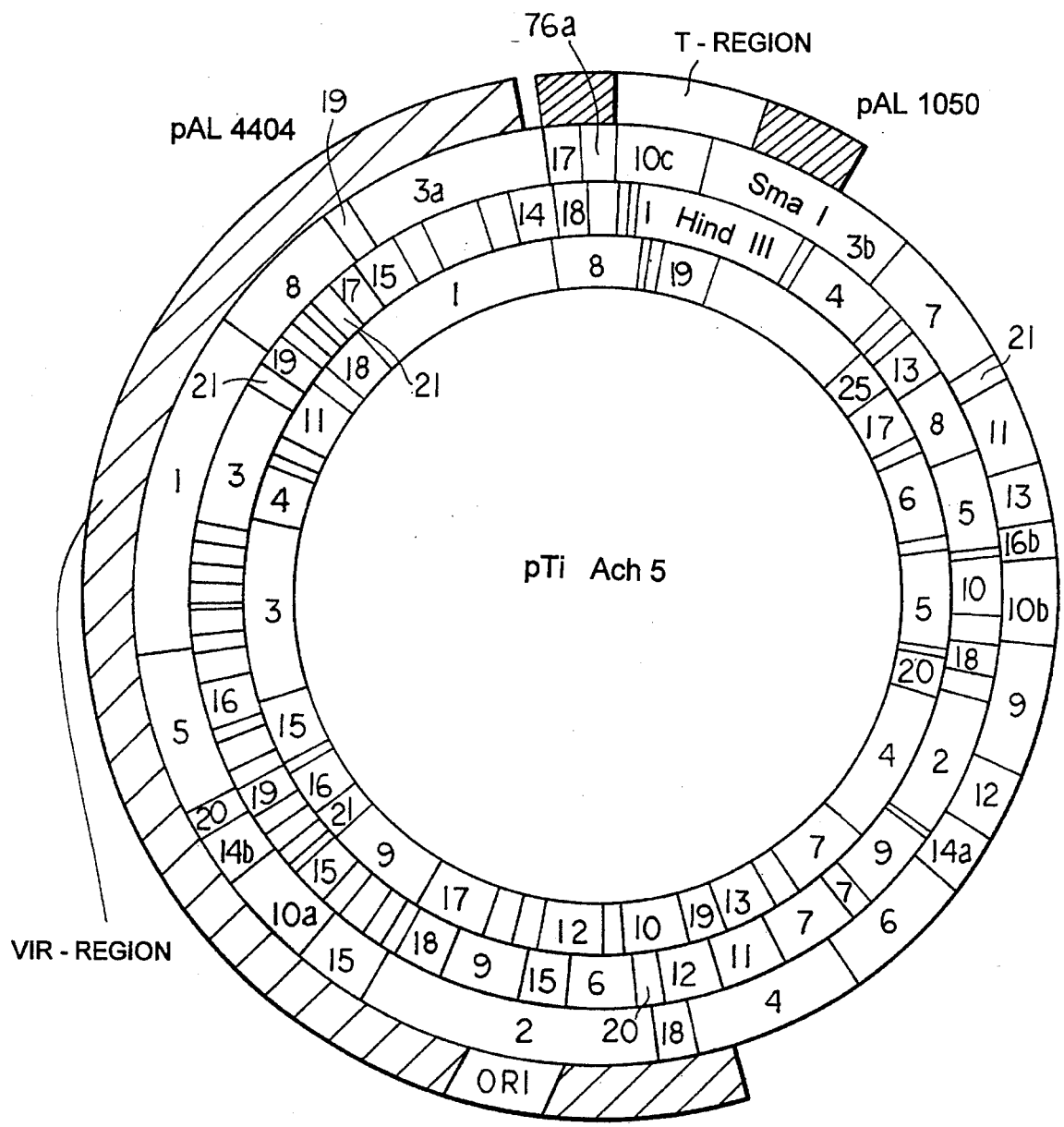
FIG. 2 shows a physical card of the plasmid pTiAch5.

The pAL1050 was transferred by conjugation into the non-oncogenous Agrobacterium strain LBA4404 (Ooms et al, Gene 14, 33–50 (1981)), which contained a strongly reduced Ti plasmid, which was lacking the whole T-region but still had an intact vir-region (vide FIG. 2). FIG. 2 shows a card of the plasmid pTIAch5, in which the T-region present on pAL1050 has been blackened and the part present on pAL4404 containing the vir-region is hatched.

The capacity of tumour induction of the transconjugant strain LBA4434, which contained both the plasmid pAL1050 with T-region and the plasmid pAL4404 with vir-region, was tested with different plant species. It appeared that the strain LBA4434 induced normal tumours on all plants investigated, in which tumours octopine could be detected (vide the table).

TABLE

| | Plant tumour induction tests | | | | | | | |
|---|---|---|---|---|---|---|---|---|
| | tomato | | kalanchoë | | tobacco | | green pea | |
| Strain plasmids | tumour | ocs* | tumour | ocs | tumour | ocs | tumour | ocs |
| LBA4001 Cr**, pTiAch5 | + | + | + | + | + | + | + | + |
| LBA4404 Cr, pAL4404 | − | | − | | − | | − | |
| LBA1050 Cr, pAL1050 | − | | − | | − | | − | |
| LBA4434 Cr, pAL1050 pAL4404 | + | + | + | + | + | + | + | + |

\* = ocs = octopine synthesis in the tumour, detected according to Otten and Schilperoort, Biochem. Biophys. Acta 527, 497–500 (1978)
\*\* = Cr = the large cryptic plasmid of A. tumefaciens strain Ach5.

These experiments show that the vir-region and the T-region of the octopine Ti plasmid can be separated physically on different plasmids without the tumour inducing capacity of the bacterium being affected by it. Since A. tumefaciens with only the plasmid pAL1050 cannot induce tumours, the results found show that these genes of the vir-region are active during transfer of the T-region to the plant cell.

One could think that the oncogenity of the Agrobacterium strain LBA4434 may be caused by the formation of a cointegrate plasmid between pAL4404 and pAL1050 in a small portion of the bacteria. However, this is not very likely for the following reasons. First of all by hybridisation experiments on Southern blots it was shown that there is no homology between the two plasmids. Consequently it is excluded that by homologous recombination between both plasmids a cointegrate is formed. Secondly, by crossing of LBA4434 (with the plasmids pAL1050 and pAL4404) with LBA4078, an A. tumefaciens strain cured of the Ti plasmid and being erythromycin resistant as receiving bacterium, no cotransfer of the non-conjugative plasmid pAL4404 with the Inc-P plasmid pAL1050 was detected (frequency lower than $10^{-4}$), from which it follows that no cointegrate formation by non-legitimate recombination had taken place or only at a very low frequency. This implies that by cointegrate formation, if any, no significant contribution to the tumour induction can have been made. For, wound infections with mixtures of oncogenous and non-oncogenous A. tumefaciens strains in low ratios do not lead to tumour formation (Lippincott et al, J. Bact. 97, 620–628 (1969)) as a result of competition between the bacteria for a restricted number of attachments sites on the plant cells. The tumours induced by LBA4434, however, are as big as those which are induced by the wild type strain Ach5. This makes it extremely unlikely that the tumour induction by LBA4434 is caused by a mixed cell population substantially consisting of non-oncogenous cells and only containing a very limited number of cells with a cointegrate plasmid.

Figure 3:
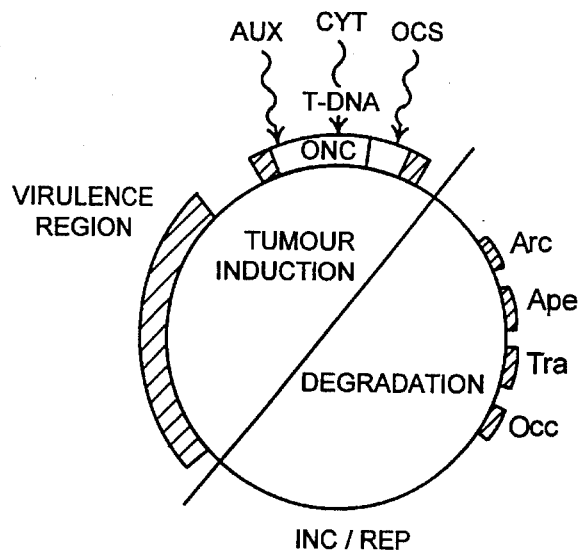
FIG. 3 shows in outline an octopine Ti plasmid.

FIG. 3 gives a picture of an octopine Ti plasmid, subdivided in a part responsible for tumour induction and a part responsible for the catabolism of octopine (octopine catabolism gene Occ) and arginine (arginine catabolism gene Arc). Tra, Inc. and Rep are functions for respectively conjugation, incompatibility and replication. Aux, Cyt and Ocs are loci for respectively auxine and cytoquinine-like effects and for octopine synthesis in the tumour cell.

Figure 4:
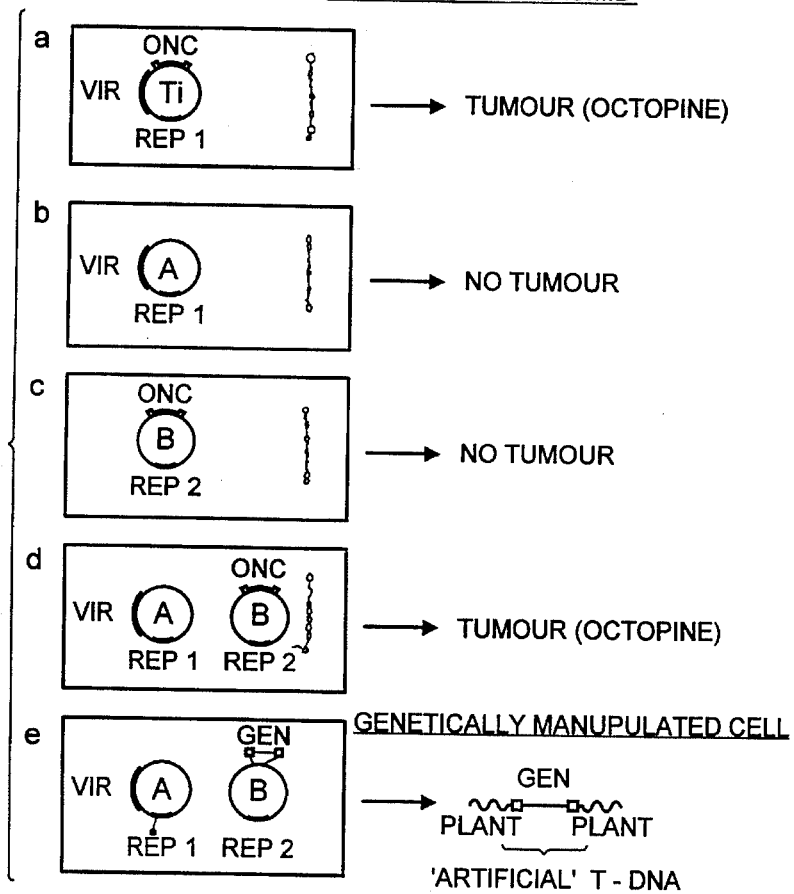
FIG. 4 shows in outline the invention.

FIG. 4a shows in outline the tumour induction which is caused by infection of plants or incubation of plant protoplasts with A. tumefaciens bacteria which contain an intact Ti plasmid.

FIGS. 4b and 4c show that both A. tumefaciens bacteria, which only contain a plasmid A without T-region (FIG. 4b) and A. tumefaciens bacteria, which only contain a plasmid B without vir-region (FIG. 4c) have no tumour inducing capacity.

FIG. 4d shows that tumour induction is possible indeed of the bacteria contain both plasmids simultaneously.

FIG. 4e shows the process according to the invention, in which use is made of A. tumefaciens bacteria which contain both a plasmid A with vir-region but without T-region, and a plasmid B with genetically manipulated T-region but without vir-region; the genetically manipulated T-region is incorporated into chromosomes of the treated plant cells.

Figure 5:
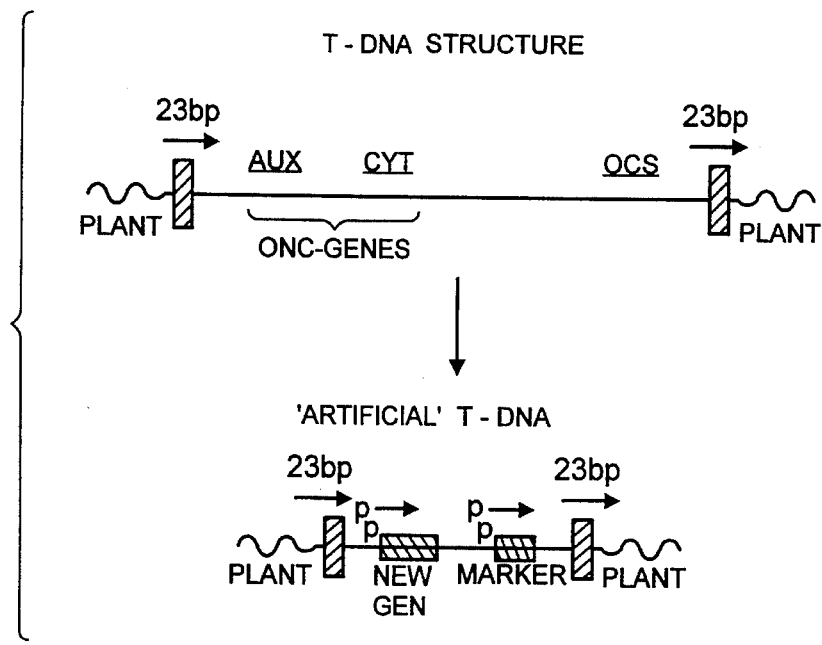
FIG. 5 shows in outline the structure of normal T-DNA and of manipulated "artificial" T-DNA, as incorporated into the plant genome; as well as with the aid of a description of performed experiments.

FIG. 5 shows in larger detail the structure of the T-region of octopine Ti plasmids, after incorporation into the plant genome. At the extremities of the T-region there is a special base sequence of about 23 base pairs (bp) which are involved in the transfer and integration of T-DNA in the plant genome. Also, an "artificial" T-DNA, incorporated into the plant genome, is shown which contains one or more desirable genes and a marker gene for the selection of transformants. In order to make expression of these genes in the plant cell possible, special base sequences are present, including a plant promotor (Pp) as a starting place for the transcription in RNA (→), which are needed for the regulation of the gene expression in eucaryots.

EXAMPLE

In order to test the suitability of the invention described in practice an experiment was carried out, in which a bacterial gene was transferred with the binary vector system to the plant cell. The gene that codes for the enzyme chloroamphenicol transacetylase, which is expressed within the bacterium, and sees to resistance of the host against the antibiotic chloroamphenicol was selected. This resistance gene is positioned on a DNA fragment which was manipulated in the plasmid pAL1050, which treatment was carried out within the host Escherichia coli. Subsequently the thus obtained plasmid derived from pAL1050, which now carries the genetic information for chloroamphenicol resistance, was transferred by means of conjugation (mating) to the Agrobacterium tumefaciens strain LBA4404, which contains a strongly reduced Ti plasmid, which was lacking the whole T-region, but did not contain an intact vir-region (vide FIG. 2). The thus obtained A. tumefaciens, with the manipulated T-region and the vir-region on separated plasmids was used for infection of a plant, in consequence of which it could be investigated whether cells were transformed in such a way that a tumour was formed having the characteristics of the presence of tumour cells with a T-DNA, in which at a known place a foreign piece of DNA is manipulated. The place of the T-region of the plasmid pAL1050, in which the earlier mentioned DNA fragment had been incorporated, had been selected in such a way that on the basis of data already known it could be expected that by transfer of the manipulated T-region to plant cells, the tumour thus formed would show the characteristic morphology of extreme adventitious root development of Kalanchoë daigremontiana and Nicotiana tabacus. The result of the infection test carried out indeed showed the expected tumour morphology, from which it may therefore be concluded that with the invention described the mentioned foreign DNA fragment was incorporated into the plant genome. This was further confirmed by Southern blot hybridisation experiments showing that the mentioned foreign DNA was incorporated in plant DNA.

Also a plurality of "artificial" T-DNA's have been constructed as is indicated in FIG. 5, where as plant marker the gene was used which codes for an enzyme called lysopine-dehydrogenase or octopine synthase. This enzyme catalyzes only when present in plant cells the synthesis of octopine by reductive condensation of arginine and pyruvate. By infection of plants in accordance with the process according to the invention tumours were induced which indeed could synthesise octopine.

The Agrobacterium strains LBA4404 and LBA1050 are deposited and available at the Centraalbureau voor Schimmel-cultures (CBS) at Baarn, the Netherlands, deposited on Feb. 24, 1983 Resp. under No. CBS 191.83 and No. 192.83.

We claim:

1. A process for incorporating into the genome of dicotyledonous plants foreign DNA, comprising infecting the plants or plant cells or incubating plant protoplasts with Agrobacterium strains, which contain plasmids, said Agrobacterium strains containing at least one plasmid having the vir-region of a Ti plasmid but no T-region, and at least one other plasmid having a T-region but no vir-region, said T-region being composed of naturally occurring border sequences consisting of about 23 base pairs at the extremities of said T-region and only foreign DNA between said border sequences, the vir-region plasmid and the T-region plasmid containing no homology which could lead to cointegrate formation.

2. Agrobacterium strains, comprising at least one plasmid having the vir-region of a Ti plasmid but no T-region, and at least one other plasmid having a T-region but no vir-region, said T-region being composed of naturally occurring border sequences consisting of about 23 base pairs at the extremities of said T-region and only foreign DNA between said sequences, the vir-region plasmid and the T-region plasmid containing no homology which could lead to cointegrate formation.

3. A process for the production of Agrobacterium strains comprising at least one plasmid having the vir-region of a Ti plasmid but no T-region, and at least one other plasmid having a T-region but no vir-region, said T-region being composed of naturally occurring border sequences consisting of about 23 base pairs at the extremities of said T-region and only foreign DNA between said border sequences, the vir-region plasmid and the T-region plasmid containing no homology which could lead to cointegrate formation, said process comprising:

(a) incorporating non-Agrobacterium foreign DNA into a plasmid having a T-region and a replicator having a broad bacterial host range, wherein said foreign DNA becomes part of the T-region, (b) cloning the resulting plasmid in Escherichia coli; and (c) introducing the resulting plasmid into Agrobacterium strains which contain at least one plasmid which has the vir-region of a Ti-plasmid but no T-region.

4. A process according to claim 1, wherein said foreign DNA comprises a gene including a plant promoter as starting place for the transcription of said gene in RNA.

5. A process according to claim 4, wherein said foreign DNA comprises in addition to said gene a marker gene for the selection of transformants, including a plant promoter as a starting place for the transcription of said marker gene in RNA.

6. A process according to claim 1, wherein the plasmid having a T-region but no vir-region is stable in said Agrobacterium strain.

7. A process according to claim 1, wherein the plasmid having a T-region but no vir-region, and the plasmid having a vir-region but no T-region do not form cointegrates at a level detectable by a bacterial conjugation test.

8. A process according to claim 1, wherein cointegration of said T-region plasmid and said vir-region plasmid do not contribute detectably to the said process.

9. A process according to claim 1, wherein frequency of cointegrate formation between said T-region plasmid and said vir-region plasmid is less than 1: 10,000.

10. A process according to claim 1, wherein said vir-region plasmid is pAL4404, as present in LBA4404, deposited under No. CBS191.83.

11. A process according to claim 1, wherein said T-region plasmid has only one right T-DNA border, and only one left T-DNA border.

12. A process for incorporating in the genome of dicotyledonous plants foreign DNA, comprising infecting the plants or plant cells or incubating plant protoplasts with Agrobacterium strains, which contain plasmids, said Agrobacterium strains containing at least one plasmid having the vir-region of a Ti-plasmid but no T-region, and at least one other plasmid having a single T-region but no vir-region, said single T-region being composed of naturally occurring border sequences at the extremities of said single T-region, the vir-region plasmid and the T-region plasmid containing no homology which could lead to cointegrate formation.

* * * * *